United States Patent [19]

Gettig

[11] Patent Number: 4,642,103
[45] Date of Patent: Feb. 10, 1987

[54] INJECTOR ASSEMBLY

[76] Inventor: William A. Gettig, Linnwood, Box 417, Millheim, Pa. 16854

[21] Appl. No.: 816,830

[22] Filed: Jan. 7, 1986

[51] Int. Cl.$^4$ .......................................... A61M 5/245
[52] U.S. Cl. .................................................. 604/234
[58] Field of Search ............... 604/234, 235, 187, 228, 604/229, 221, 232; 128/1.1

[56] References Cited

U.S. PATENT DOCUMENTS

| | | | |
|---|---|---|---|
| 1,574,579 | 2/1926 | Jones | 604/234 |
| 2,118,221 | 5/1938 | Montuori | 604/235 |
| 3,144,178 | 8/1964 | Sarnoff | 604/235 X |
| 4,122,836 | 10/1978 | Burnett | 128/1.1 |

*Primary Examiner*—John D. Yasko
*Attorney, Agent, or Firm*—Anthony A. O'Brien

[57] ABSTRACT

A syringe mechanism includes a pair of sub-assemblies one of which contains a pair of threaded connector elements. One such connector element slidably surrounds a plunger rod while the other is adapted to surround a tubular barrel of the other sub-assembly. Upon engagement and tightening of the threaded elements, a resilient sleeve disposed intermediate the barrel and its surrounding connector element, is axially fore-shortened or compressed and inwardly displaced to firmly interlock the two sub-assemblies with the forward end of the plunger rod disposed within the barrel.

12 Claims, 5 Drawing Figures

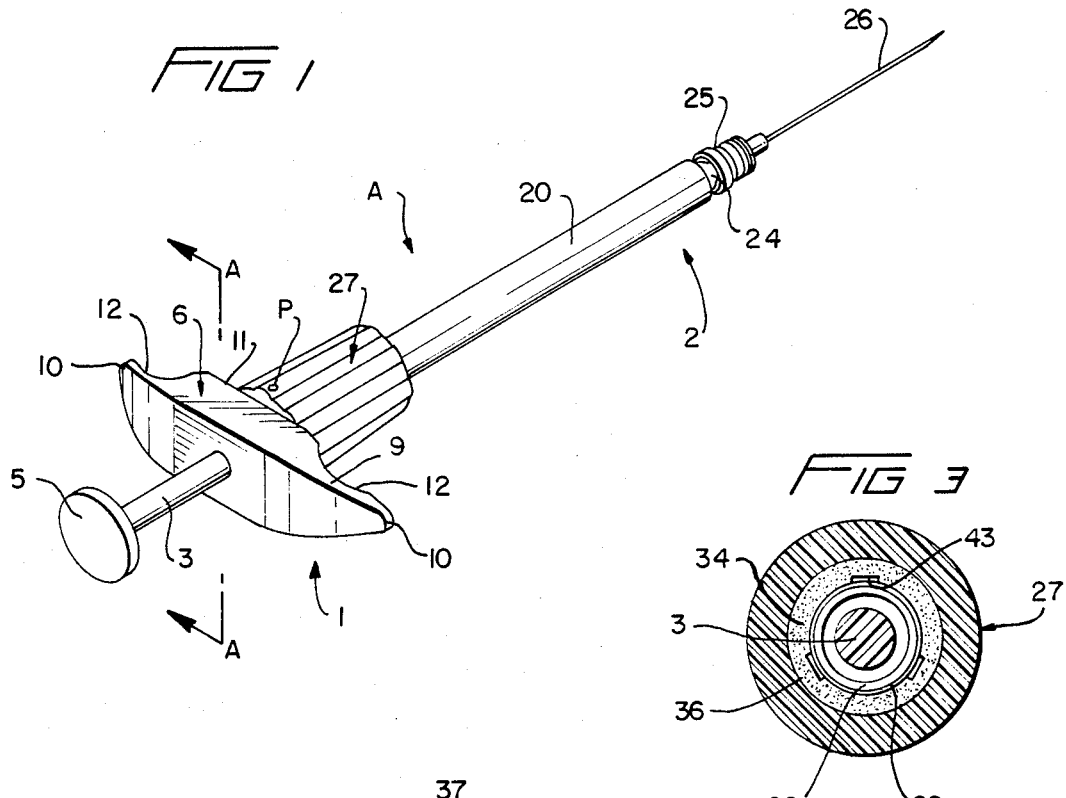
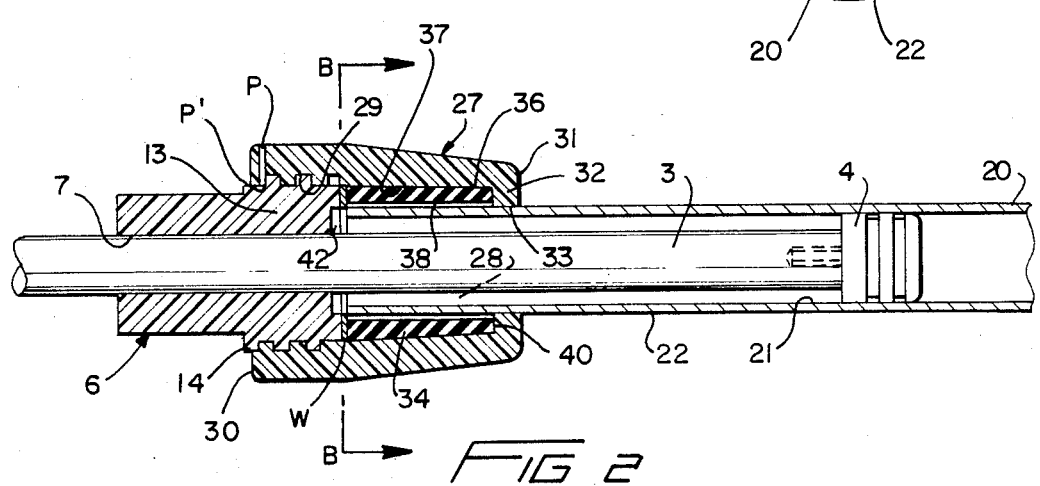
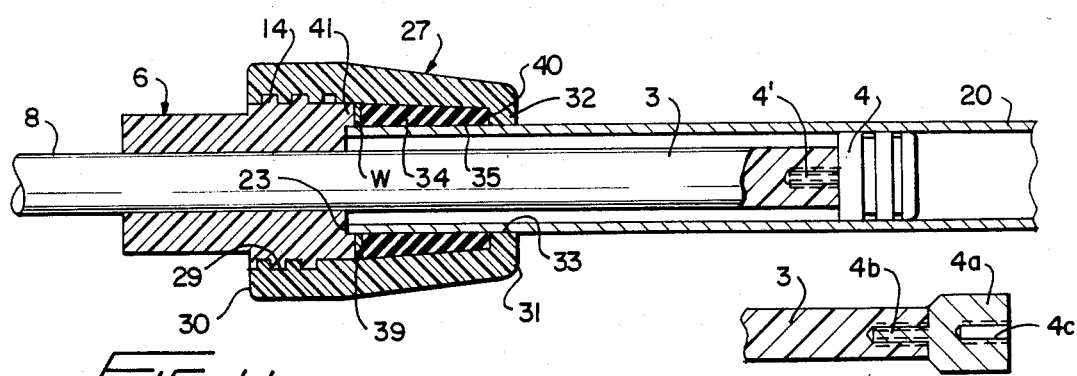

INJECTOR ASSEMBLY

BACKGROUND OF THE INVENTION

This invention relates generally to a hypodermic apparatus and more particularly to an improved injector assembly including two sub-assemblies adapted to be uniquely joined together and positively interlocked prior to use.

Two-part syringes for the injection of medicaments are well known wherein two sub-assemblies are threadedly connected to one another prior to use of the syringe. Prior art examples will be found U.S. Pat. No. 2,778,359 issued Jan. 22, 1957 to Friedman and U.S. Pat. No. 4,333,457 issued June 8, 1982 to Margulies. In both of these syringes, one of the sub-assemblies comprises a plunger rod slidably supporting a head member that is in turn, provided with either external or internal threads. This threaded member is adapted to threadedly engage mating threads formed adjacent the rear end of the syringe barrel or cartridge. To provide such a threaded connection on the cartridge sub-assembly it has been common to provide a metal or other construction at least at the rear end of the cartridge area since the cost and practicality of forming safe and reliable threads on the relatively thin stock of a conventional glass cartridge barrel rules out such latter approach.

By the present arrangement an improved cost effective syringe is provided wherein an interlocked injector assembly is offered for use with a conventional type of glass barrel. The firm interlock of the two sub-assemblies is achieved through the interaction of a first threaded connector element carried by the plunger rod and a second threaded connector element adapted to slidably surround the barrel. As the two threaded connector elements are tightened with respect to one another, a resilient or compressible sleeve contained between the second connector element and barrel is progressively axially compressed with a resultant progressive enlargement or at least radially inward displacement, thereby firmly securing the two interlock connector elements to the smooth external surface of the barrel.

Accordingly, one of the objects of the present invention is to provide an improved injector assembly including two threaded mating connector elements respectively carried by a plunger rod and adapted to surround a barrel, with a resilient member carried by one such element surrounding the external surface of the barrel and adapted to be axially compressed during interlocking of the connector elements.

A further object of the present invention is to provide an improved injector assembly including a plunger rod slidably supporting a first threaded connector element and a glass or the equivalent barrel adapted to be surrounded by a second threaded connector element and wherein with the two connector elements interlocked, a resilient sleeve captively engaged between the connector elements and the external surface of the barrel is longitudinally compressed and radially forced into a clamping action between the barrel and second connector element.

Still another object of the present invention is to provide an improved injector assembly including two threaded mating connector elements respectively carried by a plunger rod and adapted to surround a barrel, with a resilient member surrounding the external surface of the barrel and adapted to be axially compressed during interlocking of the connector elements.

A further object of the present invention is to provide an improved injector assembly including a plinger rod slidably supporting a first threaded connector element and a glass or the equivalent barrel adapted to be surrounded by a second threaded connector element and wherein with the two connector elements interlocked, a resilient sleeve captively engaged between the connector elements and the external surface of the barrel is longitudinally compressed and radially forced tolock the barrel to the second connector element.

Still another object of the present invention is to provide an improved injector assembly comprising plunger and barrel sub-assemblies each adapted to support a slidable threaded member and wherein interlocking of the two sub-assemblies is achieved without any direct threaded connection between the plunger sub-assembly and barrel.

With these and other objects in view which will more readily appear as the nature of the invention is better understood, the invention consists in the novel construction, combination and arrangement of parts hereinafter more fully described, illustrated and claimed with reference being more to the attached drawing.

BRIEF DESCRIPTION OF THE DRAWING

FIG. 1 is a perspective view of an injector assembly according to the present invention;

FIG. 2 is an enlarged longitudinal sectional view taken along the line A—A of FIG. 1;

FIG. 3 is a transverse sectional view taken along the line B—B of FIG. 2;

FIG. 4 is a view similar to FIG. 2 as the assembly appears in the fully interlocked condition; and FIG. 5 is a fragmentary longitudinal view of an alternative plunger rod end.

Similar references characters designate corresponding parts throughout the several figures of the drawing.

DESCRIPTION OF THE PREFERRED EMBODIMENTS

The present invention will be seen to comprise a hypodermic injector assembly generally designated A and which in the assembled condition such as illustated in FIG. 1, includes a first sub-assembly 1 and a second sub-assembly 2. The first sub-assembly 1 includes an elongated plunger rod 3 having an appropriate plunger or piston 4 suitably affixed at its forward end while its opposite or rearward end may be enlarged as shown in FIG. 1 to provide a head or thumb engaging member 5. The attachment of the plunger 4 may be by means of a rearwardly extending stud 4' engaging a threaded bore in the rod 3 as shown in FIG. 4. An alternative arrangement is shown in FIG. 5 wherein, a metal threaded tip 4a having a stud 4b is carried by the plunger rod 3 with this tip in turn having a threaded bore 4c for reception of the resilient plunger or piston 4. Such an arrangement has been found to exhibit improved resistance to wear as the present injector is reusable and can be autoclaved. Included in the first sub-assembly 1 is a first connecting element generally designated 6 comprising a transversely extending element provided with a central bore 7 forming a close sliding fit about the periphery 8 of the plunger rod 3.

The rear portion of the first connector element 6 is formed to provide a finger grip 9 with distal portions 10—10 diametrically extending across the bore 7. The forward or undersurface 11 of the finger grip 9 is preferably provided with concavities 12—12 for respectively receiving and engaging the fore-finger and middle finger of the user while the thumb engages the plunger rod head 5.

Extending forward of the finger grip 9 and likewise surrounding the bore 7 of the first connector element 6 is a central, cylindrical head or body 13 which from FIGS. 2 and 4 will be seen to be provided with fastener means such as external threads 14, the purpose of which will become obvious hereinafter.

The second sub-assembly 2 comprises a cartridge or barrel 20 preferably formed of the conventional glass stock having a polished or smooth innersurface 21 as well as a similar external surface 22 terminating with the flush open rear end 23. The forward end of the barrel 20 may include the usual nose 24 and optionally a hub 25 from which extends the usual cannula 26 as shown in FIG. 1 of the drawing. Normally surrounding the barrel external periphery 22 adjacent the area of the rear end 23 is a second connector element or collar 27 which will be seen to comprise a cylindrical member serving as a chuck and having an enlarged axial bore 28 extending throughout its axial extent. This bore 28 is provided with fastener means or internal threads 29 communicating with the collar rear face 30, which threads will be understood to mate with the external threads 14 associated with the first connector element 6. The front wall 31 of the collar 27 extends radially inwardly beyond the plane of the bore 28 to provide an inturned lip 32 having an inner surface 33 forming a close sliding fit about the barrel exterior 22. The chuck or second connector element 27 is preferably captively attached to the remaining structure of the first sub-assembly. This is readily achieved by means of a radially extending pin P disposed through the wall of the chuck element 27 and having an inner tip P' terminating within a groove of the threads 14 of the first connecting element 6. By locating the pin P at the rear end of the land of the threads 29, it will follow that the first connector element 6 will be precluded from separation from the second connector element 27 when threads 14 are backed out of threads 29, since the pin tip P' will abut the forward end of the groove of threads 14. To assure this abutment, the pin tip P' extends inwardly a greater amount than the adjacent threads 29. Quite obviously, other locking means may be employed to assure a positive captive relationship between the first and second connector elements but the described construction has been found to permit ready assembly of the components following which the pin P is inserted and appropriately retained, such as by epoxy adhesive.

When the two sub-assemblies 1 and 2 are separated from one another, the joined connector elements 6,27 are retained upon the plunger rod 3 by means of the head 5 at the outer end and the plunger 4 at the inner end, the diameter of both of which is substantially greater than that of the bore 7 of the connector element 6.

During joining of the two sub-assemblies 1,2, the second connector element or chuck 27 is secured about the periphery of the barrel 20 by means of a resilient, compressible member or sleeve 34 carried by the chuck and which initially slidably fits around the barrel exterior surface 22. Any suitable composition may be employed in the fabrication of the sleeve 34 such as natural or synthetic rubber. In view of the chuck inturned lip 32 it will follow that the sleeve 34 wil be retained within the first sub-assembly even when the internal surface or wall 35 of the sleeve does not surround the barrel periphery. When the first sub-assembly is initially slipped over the barrel end, the assembly A will appear in the position as shown in FIG. 2 of the drawing. The exterior surface or periphery 36 of the resilient sleeve 34 will be seen in this view to engage the inner wall 37 of the second connector element or chuck 27. In the intermediate condition of interlocking of the two subassemblies as shown in FIG. 2, only a slight peripheral clearance 38 is illustrated with this appearing between the sleeve and barrel. This clearance is exaggerated in the drawing to differentiate from the stressed condition of the sleeve following the final stage of the interlock as shown in FIG. 4.

Just prior to the final locking of the two sub-assemblies 1 and 2, the assembly A may appear as shown in FIG. 2 wherein the rear edge 39 of the cylindrial sleeve 34 is positioned slightly rearward relative the barrel rear end 23. If not initially thusly disposed, manipulation of the respective mating threads will still achieve the positive interlock of FIG. 4. In practice, the barrel rear end 23 will usually be pushed into abutment with the body 13 of the first connector element 6 but a firm interlock is achieved so long as the sleeve fully surrounds the barrel when the first sub-assembly is tightened as will be seen. In this position, the inturned lip 32 of the chuck flushly engages the forward edge 40 of the resilient sleeve 34 and while the user retains the second connector element 27 and barrel 20 in one hand, the finger grip 9 of the first connector element 6 is rotated to cause its threads 14 to engage the threads 29 of the collar 27. Prior to advancement of the first connector element threads relative the second connector element threads the assembly will appear as in FIG. 2 wherein the forward face or seat 41 of the first connector element central body 13 is in position to bear against the rear edge 39 of the resilient sleeve 34. Disposed intermediate the seat 41 and sleeve 34 is a flat washer W the inner and outer diameters of which are substantially comparable to those of the sleeve 34. This washer is fabricated from a low friction material such as nylon and serves to reduce torque on the sleeve as the first sub-assembly is tightened.

The referenced forward face 41 preferably comprises an annular ridge or shoulder projecting forwardly of a centrally disposed recess or undercut area 42, the diameter of which is no less than that of the barrel. Continued rotation of the first connector element 6 beyond the point as shown in FIG. 2 will be understood to displace the first connector element furthermore in a forward direction to the position of FIG. 4. During this latter displacement, the axial movement of the first connector element produces an axial or longitudinal compression of the resilient sleeve 34 against the stationary inturned lip or seat 32 of the second connector element 27. This axial fore-shortening of the sleeve produces a slight inward displacement of the body of the sleeve 34 and since the sleeve was already providing a close fit between the collar inner wall 37 and barrel outer wall 22, it follows that the first connector element, second connector element, and barrel will all be firmly fixed together as a unitary assembly.

With the above interlocked condition, the injector A is subsequently utilized in the conventional manner whereby the plunger rod is free to be manually withdrawn as in filling the interior of the barrel with a medicament and also usual procedures such as aspiration and injection may be accomplished. This subsequent use of the present assembly is further enhanced by the unobstructed view of blood on aspiration, an advantage not found with many existing injector assemblies.

To facilitate the frictional engagement between the inner wall 37 of the resilient sleeve 34 and the external surface 22 of the barrel 20, so as to enhance the resultant interlocking action achieved during compression of the sleeve, the interior surface 35 thereof may be provided with a plurality of grooves 43 such as shown in FIG. 3 of the drawing. If employed, at least three such grooves are formed in the sleeve and these may extend either axially or spirally throughout the extent of the sleeve. Alternatively, a plurality of ridges or lands may be substituted for the grooves 43. The provision of any such grooves is entirely optional since numerous compositions are available to provide sleeves exhibiting adequate frictional and compressive properties suitable for the present purposes.

Re-use of the first sub-assembly is possible simply by separating it from the second sub-assembly prior to autoclaving. Upon unscrewing the two connector elements 1 and 2, the existing axial pressure upon the sleeve 34 is released with a concurrent relaxation of the compressed radial force, such that the second sub-assembly barrel 20 may be free.

With the foregoing structure in mind, it will be seen that a unique multi-part injector assembly is provided wherein two encircling members normally slidable upon a glass barrel and plunger rod respectively, are adapted for threaded engagement with one another and provide, through an intermediate compressible sleeve, a firm interlocking of the encircling members relative the barrel.

I claim:

1. An injector assembly including, first and second sub-assemblies adapted to be removably affixed to each other, said first sub-assembly provided with first and second connector elements having mating fastener means, a plunger rod slidably sourrounded by said connector elements, said second sub-assembly including a barrel having a rear end and an opposite nose supporting a cannula, said barrel rear end initially slidably insertable within said second connector element, a resilient sleeve disposed intermediate said barrel and second connector element, and means on said connector elements longitudinally fore-shortening said sleeve as said connector element fastener means are engaged whereby, as said connector elements are axially displaced toward one another, said sleeve is inwardly directed to tightly interlock said two sub-assemblies.

2. An injector assembly according to claim 1 including, a plunger on one forward end of said rod and a thumb member on the opposite other end of said rod.

3. An injector assembly according to claim 1 wherein, said first connector element includes a forward central body having said fastener means thereon, a finger grip disposed outwardly of said central body, and a forwardly facing seat on said central body engageable with said sleeve.

4. An injector assembly according to claim 1 wherein, said second connector element includes a forward inturned lip defining a rearwardly facing seat engageable with said sleeve.

5. An injector assembly according to claim 1 wherein, said fastener means includes external threads on said first connector element and internal threads on said second connector element.

6. An injector assembly according to claim 1 wherein, said sleeve includes an inner wall and an external surface, a plurality of grooves in said inner wall, and the radial distance between said inner wall and external surface is less than the radial distance between said barrel and second connector element prior to said longitudinal fore-shortening of said sleeve.

7. An injector assembly according to claim 3 wherein, said second sub-assembly connector element comprises a chuck having an axial bore, and said first connector element central body having a diameter greater than said barrel and insertable within said chuck.

8. An injector assembly according to claim 3 wherein, said finger grip includes a pair of diametrically opposed distal portions each having a forwardly facing undersurface respectively provided with a concavity for engagement by a user's fingers.

9. An injector assembly according to claim 3 including, a washer disposed intermediate said seat and sleeve.

10. An injector assembly according to claim 3 including, means carried by at least one said connector element to limit the relative axial displacement between said connector elements.

11. An injector assembly according to claim 9 wherein, said washer includes an internal diameter no less than the external diameter of said barrel.

12. An injector according to claim 10 wherein, said limitmeans includes a pin carried by said second connector element and having an inner tip juxtaposed said first connector element fastener means.

* * * * *